United States Patent
Schrader et al.

(10) Patent No.: US 9,433,235 B2
(45) Date of Patent: *Sep. 6, 2016

(54) SOLUBILIZATION AGENT FOR SOLUBILIZING POLYPHENOLS, FLAVONOIDS AND/OR DITERPENOID GLUCOSIDES

(75) Inventors: Dirk Schrader, Holzminden (DE); Thomas Riess, Holzminden (DE); Cornelia Homner, Holzminden (DE); Christopher Sabater-Lüntzel, Holzminden (DE)

(73) Assignee: SYMRISE AG, Holzminden (DE)

( * ) Notice: Subject to any disclaimer, the term of this patent is extended or adjusted under 35 U.S.C. 154(b) by 159 days.

This patent is subject to a terminal disclaimer.

(21) Appl. No.: 13/574,102

(22) PCT Filed: Jan. 24, 2011

(86) PCT No.: PCT/EP2011/050904
§ 371 (c)(1),
(2), (4) Date: Sep. 5, 2012

(87) PCT Pub. No.: WO2011/089247
PCT Pub. Date: Jul. 28, 2011

(65) Prior Publication Data
US 2012/0322750 A1    Dec. 20, 2012

Related U.S. Application Data

(60) Provisional application No. 61/297,445, filed on Jan. 22, 2010.

(30) Foreign Application Priority Data

Jan. 22, 2010 (EP) .................... 10151488

(51) Int. Cl.
| A23L 1/035 | (2006.01) |
| A23L 1/22  | (2006.01) |
| A23L 2/385 | (2006.01) |
| A23L 2/52  | (2006.01) |
| A61K 8/34  | (2006.01) |
| A61K 8/37  | (2006.01) |
| A61K 8/60  | (2006.01) |
| A61K 8/63  | (2006.01) |
| A61K 8/73  | (2006.01) |
| A61K 8/97  | (2006.01) |
| A61Q 19/00 | (2006.01) |
| A61Q 19/02 | (2006.01) |
| A61Q 19/08 | (2006.01) |

(52) U.S. Cl.
CPC ............ *A23L 1/035* (2013.01); *A23L 1/22058* (2013.01); *A23L 2/385* (2013.01); *A23L 2/52* (2013.01); *A61K 8/34* (2013.01); *A61K 8/345* (2013.01); *A61K 8/375* (2013.01); *A61K 8/602* (2013.01); *A61K 8/63* (2013.01); *A61K 8/73* (2013.01); *A61K 8/732* (2013.01); *A61K 8/97* (2013.01); *A61Q 19/00* (2013.01); *A61Q 19/02* (2013.01); *A61Q 19/08* (2013.01)

(58) Field of Classification Search
None
See application file for complete search history.

(56) References Cited

U.S. PATENT DOCUMENTS 6,096,364 A * 8/2000 Bok .................. A61K 31/34
                                            424/439
2006/0153936 A1    7/2006 Tsuzaki

FOREIGN PATENT DOCUMENTS

| FR | 608302 A      | 7/1926  |           |
| JP | 63233761 A    | 9/1988  |           |
| JP | 63291979 A    | 11/1988 |           |
| JP | 1993064572 A *| 3/1993  | ........ A23L 2/38 |
| JP | 2003000195 A  | 1/2003  |           |
| JP | 2003128542 A  | 5/2003  |           |
| JP | 2004 065128 A | 3/2004  |           |
| JP | 2004091392 A  | 3/2004  |           |
| JP | 2004267041 A  | 9/2004  |           |

OTHER PUBLICATIONS

Rigano, L., Lionetti, N., & Otero, R. (2009). Quillaja Triterpenic Saponins—The Natural Foamers. SOFW—Journal, 135(4), 1-9.*
Hirokazu et al., JP 2003000195 A, Jan. 2003, machine translation. Retreived on Feb. 10, 2014 from http://dossier1.ipdl.inpit.go.jp/AIPN/odse_top_dn.ipdl?N0000=7400.*
Repollés, C., Herrero-Martínez, J. M., & Ràfols, C. (2006). Analysis of prominent flavonoid aglycones by high-performance liquid chromatography using a monolithic type column. Journal of chromatography A, 1131(1), 51-57.*

(Continued)

Primary Examiner — Eric Olson
Assistant Examiner — Dale R Miller
(74) Attorney, Agent, or Firm — Polsinelli PC

(57) ABSTRACT

Described is a solubilization agent for solubilizing polyphenols, flavonoids and/or diterpenoid glucosides in aqueous liquids, wherein the solubilization agent consists of a mixture of:
(a) one emulsifying polymer or a mixture of two, three or more emulsifying polymers,
(b) one saponin or a mixture of two, three or more saponins,
(c) one partially or fully water-miscible, preferably liquid, solvent or a mixture of partially or fully water-miscible, preferably liquid, solvents, preferably selected from the group consisting of ethanol, propylene glycol (1,2-propanediol), glycerin, triacetin (glycerin triacetate), diacetin (glycerin diacetate) and triethyl citrate,
and
(d) water.
The solubilization agent is particularly suitable for sparingly water soluble polyphenols, flavonoids and/or diterpenoid glucosides. The invention also relates to compositions and (food or cosmetic) formulations comprising said solubilization agent. It further relates to a method for producing solubilization agents, compositions and (food or cosmetic) formulations.

4 Claims, No Drawings

(56) References Cited

OTHER PUBLICATIONS

Mahendran, T., Williams, P. A., Phillips, G. O., Al-Assaf, S., & Baldwin, T. C. (2008). New Insights into the Structural Characteristics of the Arabinogalactan-Protein (AGP) Fraction of Gum Arabic. Journal of agricultural and food chemistry, 56(19), 9269-9276.*

Hayashi et al., JP 2004091392 A, Mar. 2004, machine translation, Retreived on Sep. 2, 2015 from http://worldwide.espacenet.com.*

Yasuo et al., JP H0564572 A, Mar. 1993, machine translation, Retreived on Sep. 2, 2015 from http://worldwide.espacenet.com.*

Database WPI Week 200420 Thomson Scientific, London, GB; AN 2004-209130 XP002590905, & JP 2004 065128 A (Maruzen Seiyaku KK) Mar. 4, 2004, abstract.

Schopke T.H. et al., "Effects of saponins on the water solubility of quercetihn," Die Pharmazie, Govi Verlag Pharmazeutischer Verlag GmbH, Eschborn, DE, vol. 52, No. 3, Mar. 31, 1997, pp. 232-234, XP002981324.

International Search Report with references cited and Written Opinion under Rule 43 PCT attached to the Search Report, International Application No. PCT/EP2011/050904.

* cited by examiner

SOLUBILIZATION AGENT FOR SOLUBILIZING POLYPHENOLS, FLAVONOIDS AND/OR DITERPENOID GLUCOSIDES

CROSS REFERENCE TO RELATED APPLICATIONS

This application is a National phase filing under 35 U.S.C. §371 of International Application No. PCT/EP2011/050904, filed Jan. 24, 2011, which claims priority to European Application No. 1015488.3 and U.S. Provisional Application No. 61/297,445, both filed on Jan. 22, 2010. The entire contents of each of the above-applications are incorporated herein by reference.

The present invention relates to a solubilization agent, perferably suitable for sparingly water soluble polyphenols, flavonoids and/or diterpenoid glucosides, and to compositions and (food or cosmetic) formulations comprising said solubilization agent. It further relates to a method for producing solubilization agents, compositions and (food or cosmetic) formulations according to the present invention. It also relates to a method for imparting, enhancing and/or modifying the properties of a polyphenol, flavonoid and/or diterpenoid glucoside.

Polyphenols, flavonoids and/or diterpenoid glucosides are used in foods and cosmetics for several reasons, e.g. to improve the healthiness, for masking off-notes, for enhancement of sweetness or for imparting certain cosmetic effects.

For example, polyphenols, flavonoids and/or diterpenoid glucosides are known to have sweet-tasting, sweetness-enhancing, bitterness-reducing, skin-tanning or skin-lightening properties.

However, many polyphenols, flavonoids and/or diterpenoid glucosides are poorly soluble in water or aqueous liquids. In addition, in particular when used in (aqueous) foods, beverages or (aqueous) cosmetics, polyphenols, flavonoids and/or diterpenoid glucosides tend to precipitate. In (aqueous) foods or beverages, precipitation is often causing changes of taste and/or is detrimental to the efficacy of the polyphenols, flavonoids and/or diterpenoid glucosides. Precipitation or recrystallization for example occurs during (prolonged) storage is particularly a disadvantage in the case of (clear) food or cosmetic compositions, in particular in the case of beverages.

Clear beverages have to be stable for several months or even for years and a sediment caused by the precipitation of polyphenols, flavonoids and/or diterpenoid glucosides often is repulsive to consumers.

US 2009/0004304 and US 2008/0102131 describe compositions comprising an oil component, a water soluble polymer, a saccharide and a surfactant. Examples are given for aqueous emulsion compositions comprising gum Arabic, licorice polyphenols and lecithin. In the list of surfactants, saponins are mentioned.

EP 2 085 097 discloses a composition comprising gum Arabic, water and quillaja saponin and CoQ10. The ingredients were mixed by using a high pressure homogenizer yielding an emulsion.

Compositions for the solubilization of compounds are described in US 2009/280987 and WO 2007/051329, in which the stabilization is realized by using non-food grade poloxamers, not being applicable for beverages and other foodstuffs.

WO 2008/034273 and WO 2008/138155 describe a method to solubilize oil-soluble vitamins or fats to form a clear solution by spontaneous micelle formation using gum Arabic or gum Arabic and wood resins. These kind of micellar solutions or microemulsions can be formed using different surfactants to form extremely small oil droplets but not stabilizing oil and water-insoluble substances like polyphenols and flavonoids. Additionally the use of wood resins is often not allowed in clear beverages.

WO 2007/122251 proposes to improve the solubility and/or stability of glycosyl flavanones by mixing the glycosyl flavanones with maltodextrin or mixtures of maltodextrin and gum arabic as carriers and subsequent spray-drying of said mixture.

The compositions or emulsions comprising polyphenols, flavonoids and/or diterpenoid glucoside of the prior art do not solve the problem of precipitation or recrystallization of (sparingly water-soluble) polyphenols, flavonoids and/or diterpenoid glucosides occurring during (prolonged) storage of a food or cosmetic formulation in a satisfactory manner or not to a sufficient extent. In addition, it would be desirable to include higher amounts of polyphenols, flavonoids and/or diterpenoid glucosides into food or cosmetic formulations, in order to obtain (enhanced) efficacy of the properties of the polyphenols, flavonoids and/or diterpenoid glucosides.

It was therefore one object of the present invention to stabilize, in particular sparingly water soluble, polyphenols, flavonoids and/or diterpenoid glucosides against precipitation in beverages, foods, perfumes or cosmetics. Preferably, the stabilization should last for several weeks, preferably for at least 6 months.

In a first aspect, the present invention relates to a solubilization agent for solubilizing polyphenols, flavonoids and/or diterpenoid glucosides in aqueous liquids, wherein the solubilization agent consists of a mixture of:

(a) one emulsifying polymer or a mixture of two, three or more emulsifying polymers, (b) one saponin or a mixture of two, three or more saponins, (c) one partially or fully water-miscible, preferably liquid, solvent or a mixture of partially or fully water-miscible, preferably liquid, solvents, preferably selected from the group consisting of ethanol, propylene glycol (1,2-propanediol), glycerin, triacetin (glycerin triacetate), diacetin (glycerin diacetate) and triethyl citrate, and (d) water.

The solubilization agents according to the invention allow for an improved (i.e. higher) solubility of polyphenols, flavonoids and/or diterpenoid glucosides, in particular of the sparingly water soluble polyphenols, flavonoids and/or diterpenoid glucosides (as defined below), in aqueous liquids, in particular in liquids having a water content of 50 wt. % or more, more preferably having a water content of 60 wt. % or more.

This is a particular advantage when the solubilization agents according to the invention are used to produce beverages, foods, perfumes or cosmetics, and is especially useful for producing of storage stable (food and cosmetic) formulations, preferably clear beverages. The solubilization agents also prevent precipitation or recrystallization of (sparingly water soluble) polyphenols, flavonoids and/or diterpenoid glucosides, as for example occurs during (prolonged) storage, thus the compositions and formulations according to the present invention, as described in more detail below, allow an increased solubilization of polyphenols, flavonoids and/or diterpenoid glucosides in aqueous liquids, in particular in food and cosmetic formulations. Additionally, the compositions, food and cosmetic formulations show an improved storage stability (shelf life).

Solubilization agents in accordance with the present invention may be obtained as described below. The skilled artisan may easily arrive at solubilization agents according to the present invention by varying the parameters based on his general knowledge and taking guidance from the teaching in the present text, in particular in the description of preferred embodiments, the examples and the claims.

It was also observed—in contrast to the typical disadvantageous behaviour of saponins—that when (quillaic) saponins were used as part of a solubilization agent, composition or (food or cosmetic) formulation in accordance with the present invention, a strongly reduced or even virtually no foaming of the saponins was observed.

Without wishing to be bound by theory, the present inventors believe that the solubilization agents of the present invention are obtained in form of a complex of components (a), (b), and (c), i.e. the emulsifying polymer(s), saponin(s) and the partially or fully water-miscible solvent(s). Water as component (d) is used to dissolve the emulsifying polymer(s) and the saponin(s), at least to such an extent that components (a) and (b) may come in contact and form the complex.

The solubilization agents of the present invention improve and increase the soluble amount of polyphenols, flavonoids and/or diterpenoid glucosides in an aqueous liquid or in water and stabilize the polyphenols, flavonoids and/or diterpenoid glucosides in the final product, preferably in (food or cosmetic) formulations, particularly in beverages.

According to the present invention, said one emulsifying polymer or one, two, three or more emulsifying polymers of component (a) are preferably selected from the group consisting of edible water soluble polymers, preferably selected from the group consisting of gum Arabic, modified starch, pectin, traganth gum and gum Ghatti, more preferably from the group consisting of gum Arabic and modified starch. Most preferred is gum Arabic, since with this emulsifying polymer the highest solubility and (precipitation/recrystallization) stability of the polyphenols, flavonoids and/or diterpenoid glucosides was achieved.

According to the present invention, said saponin or one, two, three or more saponins of component (b) are preferably selected from the group consisting of quillaic saponins, since quillaic saponins allow the highest solubility and (precipitation/recrystallization) stability of polyphenols, flavonoids and/or diterpenoid glucosides investigated in the context of the present invention.

Saponins may be obtained from vegetable plants such as e.g. tomatoes, potatoes, soy beans as well as herbs and teas. Preferably, the saponins are selected from the quillaic acid saponins. Quillaic acid saponins according to the invention are saponins comprising quillaic acid as the aglycone. Quillaic acid saponins may be obtained from the bark of the so called "soap bark tree", also called *Quillaja saponaria molina* and sometimes *Quillaja saponaria*. Most preferably the saponins according to the invention are part of an extract from the bark of the soap bark tree. Preferred extracts used in accordance with the present invention are aqueous, preferably obtained by aqueous extraction of the bark.

Preferably, in the context of the present invention a saponin extract, preferably an extract of quillaic acid saponins, is used in the form of an aqueous extract having a content of triterpenic saponins in the range of from 2 to 50 wt. %, preferably in the range of from 5 to 35 wt. %, most preferably in the range of from 10 to 25 wt. %, based on the total mass of the aqueous saponin extract.

Quillaja saponins are natural tensoactives (or surfactants) derived from the tree *Quillaja saponaria*, indigenous to Chile. They have been used for over 100 years as foaming agents in food and beverages, production of photographic films, adjuvants in animal vaccines, and also in cosmetics.

The extract of quillaia is used in the manufacture of food additives (number E999). It is used as in baked goods, frozen dairy products, and puddings and as a foaming agent in soft drinks. It also applied in some "natural" spray adjuvant formulations for agricultural uses.

Quillaja saponins are non ionic surfactants, resistant to salt, heat, and extremely stable to acid pH. Chemically they consist of a triterpene, with sugar chains in carbons 3 and 28. Different sugar chains give rise to at least 50 different types of quillaja saponins. Molecular weight is of 1300-2600 Dalton. The molecular weight of preferred quillaja saponins in compositions of the present invention is 1800-2600 Dalton. Particularly preferred is the range from 1800-2000 Dalton. Below 200-500 ppm saponins exist as monomers; above 200-500 ppm they aggregate as micelles, with a molecular weight of approximately 100.000 Dalton.

Regarding the structural elucidation and classification of Quillaja saponins, reference is made to the Thesis of Johan Bankefors, 2006, Uppsala, Sweden, ISBN 91-576-7181-8.

The purification of several Quillaja saponins is described in U.S. Pat. No. 5,057,540 and U.S. Pat. No. 5,817,314.

According to the present invention, the weight ratio of component (a) to component (b) is in the range of from 20:1 to 1:2, preferably of from 12:1 to 1:1, more preferably of from 10:1 to 2:1.

The ratios are preferred, because agents, compositions and formulations according to the present invention comprising component (a) to component (b) in these ratios have shown to have better effects in terms of solubility and (precipitation/recrystallization) stability of the polyphenols, flavonoids and/or diterpenoid glucosides.

According to the present invention, the one or more partially or fully water-miscible solvents of component (c) are preferably liquid (at 25° C. and 1013 mbar), and are more preferably selected from the group consisting of ethanol, propylene glycol (1,2-propanediol), glycerin, triacetin (glycerin triacetate), diacetin (glycerin diacetate) and triethyl citrate.

More preferably, the one or more solvents of component (c) are fully water-miscible solvents and are preferably selected from the group consisting of ethanol and propylene glycol (1,2-propanediol). Most preferred is propylene glycol, since with this water-miscible solvent the best effects regarding solubility and (precipitation/recrystallization) stability of the polyphenols, flavonoids and/or diterpenoid glucosides is achievable.

The present invention also relates to a solubilization agent, wherein the agent can be prepared by a method comprising the following steps:
  providing as component (a) one emulsifying polymer or a mixture of two, three or more emulsifying polymers,
  providing as component (b) one saponin or a mixture of two, three or more saponins
  providing as component (c) one partially or fully water-miscible, preferably liquid, solvent or a mixture of partially or fully water-miscible, preferably liquid, solvents, preferably selected from the group consisting of ethanol, propylene glycol (1,2-propanediol), glycerin, triacetin (glycerin triacetate), diacetin (glycerin diacetate) and triethyl citrate,
and
  providing as component (d) water,
  mixing, preferably dissolving, component (a) and component (b) in components (c) and (d), so that an (clear)

aqueous mixture, preferably a clear solution, comprising components (a), (b), (c) and (d) is obtained.

The present invention also relates to a method of preparing a solubilization agent according to the present invention, comprising the following steps:

providing as component (a) one emulsifying polymer or a mixture of two, three or more emulsifying polymers, providing as component (b) one saponin or a mixture of two, three or more saponins providing as component (c) one partially or fully water-miscible, preferably liquid, solvent or a mixture of partially or fully water-miscible, preferably liquid, solvents, preferably selected from the group consisting of ethanol, propylene glycol (1,2-propanediol), glycerin, triacetin (glycerin triacetate), diacetin (glycerin diacetate) and triethyl citrate, and providing as component (d) water, mixing, preferably dissolving, component (a) and component (b) in components (c) and (d), so that an (clear) aqueous mixture, preferably a clear solution, comprising components (a), (b), (c) and (d) is obtained.

In a further aspect, the present invention relates to a composition comprising (i) one, two, three or more ingredients selected from the group consisting of polyphenols, flavonoids and/or diterpenoid glucosides, preferably one, two, three or more sparingly or non-water soluble polyphenols, flavonoids and/or diterpenoid glucosides, optionally (ii) water, additionally to the water comprised in component (iv), optionally (iii) one partially or fully water-miscible, preferably liquid, solvent or a mixture of partially or fully water-miscible, preferably liquid, solvents, preferably selected from the group consisting of ethanol, propylene glycol (1,2-propanediol), glycerin, triacetin (glycerin triacetate), diacetin (glycerin diacetate) and triethyl citrate, additionally to the one or more partially or fully water-miscible solvents comprised in component (iv), (iv) a solubilization agent according to the present invention, in an amount effective to increase the solubility of one or more ingredients of component (i), optionally (v) an organic acid, and optionally (vi) a preserving agent.

In some preferred cases, the one, two, three or more ingredients selected from the group consisting of polyphenols, flavonoids and/or diterpenoid glucosides of component (i) are used as such, i.e. in pure, undiluted form, in particular without dilution with components (ii) or (iii), added to the solubilization agent of component (iv), and subsequently mixed.

In some cases it has shown to be advantageous for compositions according to the present invention to mix or dissolve the polyphenols, flavonoids and/or diterpenoid glucosides of component (i) in one or more partially or fully water-miscible solvents of component (iii) before combining, preferably mixing, with a solubilization agent of component (iv).

Thus, in some cases, the one or more partially or fully water-miscible solvents of optional component (iii) are preferably liquid (at 25° C. and 1013 mbar), more preferably selected from the group consisting of ethanol, propylene glycol (1,2-propanediol), glycerin, triacetin (glycerin triacetate), diacetin (glycerin diacetate) and triethyl citrate.

More preferably, the one or more solvents of optional component (iii) are fully water-miscible solvents and preferably selected from the group consisting of ethanol and propylene glycol (1,2-propanediol), propylene glycol being most preferred.

Preferred compositions according to the present invention comprise one or more organic acids as component (v), preferably selected from the group consisting of malic acid, citric acid, acetic acid, lactic acid, more preferably the organic acid(s) of component (v) is or comprises citric acid.

Preferred compositions according to the present invention comprise one or more preservating agents as component (vi), preferably selected from the group consisting of sorbates and benzoates and more preferably from potassium sorbate and/or sodium benzoate.

Preferably, a composition according to the present invention is a clear solution.

The term "clear" in the context of the present invention refers to a composition of matter having a turbidity of less than 10 FNU (Formazin Nephelometric Units) as measured according to DIN EN ISO 7027-Water quality-Determination of turbidity (ISO 7027:1999).

Preferably, a composition and in particular a (food) formulation according to the present invention has a turbidity of less than 5 FNU, preferably measured with a Hach Turbidimeter 2100N IS.

Preferably, a composition according to the present invention is a clear solution which, when stored without agitation at 25° C. and 1013 mbar, remains clear for at least 1 week, preferably at least 2 weeks, more preferably at least 3 weeks, even more preferably at least 4 weeks, most preferably 6 months and particularly preferred at least 1 year.

Sparingly water soluble polyphenols, flavonoids and/or diterpenoid glucosides according to the invention have a solubility in water of below 1000 mg/l, preferably 50 mg/l and particular preferably below 30 mg/l and most preferred between 0.001 and 10 mg/l at 20° C.

Preferred compositions according to the present invention are those in which component (i) consists of one, two or more sparingly soluble ingredients selected from the group consisting of polyphenols, flavonoids and/or diterpenoid glucosides with a solubility in water at 20° C. of below 1000 mg/l, preferably 50 mg/l, more preferably 30 mg/l, and most preferably between 0.001 and 10 mg/l, and optionally one or more further ingredients selected from the group consisting of polyphenols, flavonoids and/or diterpenoid glucosides, and wherein component (iv) is present in an amount effective to increase the solubility of one, more or all of said sparingly soluble ingredients of component (i).

Polyphenols preferably used in the context of the present invention are sweetness-enhancing polyphenols, in particular those described in WO 2007/014879 and WO 2007/107596. Among the polyphenols, hesperetin and phloretin are particularly preferred.

Flavonoids preferably used in the context of the present invention are bitterness-reducing polyphenols, in particular those described EP 1 258 200 A2.

Flavonoids in the context of the present invention also include flavonoid glycosides. Preferred flavonoids used in the context of the present invention are skin-tanning or skin-lightening agents, preferably glycosyl flavanones, and in particular the skin-tanning flavonoids described in WO 2006/045760.

Among the flavonoids, (bitterness-reducing) homoeriodictyol and (skin-tanning) naringin are particularly preferred.

Diterpenoid glucosides, preferably used in the context of the present invention, are sweet-tasting or sweetness-enhancing diterpenoid glucosides, in particular those described in Natural Product Reports 1993, 301-309. Among the diterpenoid glucosides, rubusosides, in particular rubusoside, are particularly preferred.

Preferred polyphenols, flavonoids and/or diterpenoid glucosides according to the invention thus are hesperetin, phloretin, homoeriodictyol, rubusoside and naringin.

Thus, preferred compositions according to the present invention are those in which
component (i) consists of
one, two or more sparingly soluble ingredients selected from the group consisting of phloretin, hesperetin, homoeriodictyol, rubusoside and naringin, and
optionally one or more further ingredients selected from the group consisting of polyphenols, flavonoids and/or diterpenoid glucosides,
and wherein
component (iv) is present in an amount effective to increase the solubility of one or more of said sparingly soluble ingredients of component (i).

In a preferred embodiment of the invention the emulsifying polymer(s) of component (a), the saponin(s) of component (b), the partially or fully water-miscible solvent(s) of component (c) and water form a synergistic mixture enabling an improved solubility and/or (precipitation/recrystallization) stability of the polyphenols, flavonoids and/or diterpenoid glucosides of component (i).

Also preferred compositions according to the present invention are those in which
the weight ratio of component (a) to component (b) within composition component (iv) is in the range of from 20:1 to 1:2, preferably of from 12:1 to 1:1, more preferably of from 10:1 to 2:1,
and
the weight ratio of the sum of the total amounts of components (a) and (b) of composition component (iv) to the total amount of component(s) (i) is in the range of from 10:1 to 1:2, preferably 5:1 to 1:1.

A particularly preferred composition according to the present invention, which is particularly suitable for the preparation of (clear) beverage formulations, comprises or consists of:
(i) one, two, three or more polyphenols, flavonoids and/or diterpenoid glucosides selected from the group consisting of hesperetin, phloretin, homoeriodictyol, rubusoside and naringin,
(iv) a solubilization agent comprising (a) gum Arabic, (b) quillaic saponins, (c) propylene glycol and (d) water, preferably in the preferred amounts and ratios indicated hereinbefore or hereinafter, in an amount effective to increase the solubility of one or more ingredients of component (i),
(v) citric acid,
and
optionally (vi) potassium sorbate and/or sodium benzoate.

The above mentioned (particularly) preferred aspects and embodiments relating to a solubilization agent according to the present invention and a composition according to the present invention also apply to (particularly) preferred aspects and embodiments (food, preferably beverage) formulations, uses and methods in accordance with the present invention.

The present invention also relates to a method of preparing a composition, preferably a preferred composition according to the present invention, comprising the following steps:

providing as component (iv)
a solubilization agent (prepard) according to the present invention, in an amount effective to increase the solubility of one or more ingredients of component (i),
providing as component (i)
one, two, three or more ingredients selected from the group consisting of polyphenols, flavonoids and/or diterpenoid glucosides, preferably one, two, three or more sparingly or non-water soluble polyphenols, flavonoids and/or diterpenoid glucosides,
wherein component (i) optionally is provided in form of a solution or mixture comprising as component (iii)
one partially or fully water-miscible, preferably liquid, solvent or a mixture of partially or fully water-miscible, preferably liquid, solvents, preferably selected from the group consisting of ethanol, propylene glycol (1,2-propanediol), glycerin, triacetin (glycerin triacetate), diacetin (glycerin diacetate) and triethyl citrate,
mixing component (iv) and component (i),
optionally adding as component (ii)
water.

In some cases, the method of preparing a composition according to the present invention comprises the following steps:
providing a solubilization agent according the present invention
heating the solubilization agent to a temperature in the range of from 40 to 120° C., preferably in the range of from 50 to 98° C., more preferably in the range of from 60 to 90° C.,
adding component (i) polyphenols, flavonoids and/or diterpenoid glucosides as such, e.g. in solid or crystalline form, to the heated solubilization agent, i.e. in the absence of (further) diluents in component (i), in particular without diluting component (i) with components (ii) and/or (iii),
mixing all components.

Preferably, said mixing is conducted such that component (i) is completely dissolved.

Preferably, the method of preparing a composition according to the present invention comprises the following steps:
preparing a first solution comprising component (i) (i.e. polyphenols/flavonoids/difergenoid glucosides) and component (iii) (i.e. solvent),
preparing a second solution comprising components (a) (i.e. emulsifying polymer(s)) and (b) (i.e. saponin(s)) of component (iv) (i.e. solubilization agent) and component (ii) (i.e. water), optionally including component (c) of component (iv), and
mixing said first and second solution.

In the step of preparing said first solution, the temperature preferably is in the range of from 5 to 120° C., more preferably in the range of from 20 to 100° C. and most preferably in the range of from 70 to 90° C.

In the step of preparing said second solution, the temperature preferably is in the range of from 5 to 98° C., more preferably in the range of from 10 to 80° C. and most preferably in the range of from 10 to 40° C.

In the step of mixing said first and second solution, the temperature preferably is in the range of from 5 to 120° C., more preferably in the range of from 10 to 98° C. and most preferably in the range of from 10 to 40° C.

The method of preparing a composition in accordance with the present invention may be carried out using the following procedure:

dissolving the polyphenols, flavonoids and/or diterpenoid glucosides of component (i) in solvent (c) to form a first solution, dissolving the emulsifying polymer (a) and the saponines (b) in water (d) to form a second solution, and combining and mixing said second solution and said first solution.

Preferably, shear forces during mixing should be low in order to obtain a complete solution of the ingredients. Surprisingly it has been observed by the inventors that using relatively low shear forces in step 3 (mixing of first and second solution) results in a complete solution of the sparingly water soluble polyphenols, flavonoids and/or diterpenoid glucosides while using very high shear forces or high pressure homogenization resulted in precipitation in the final food or cosmetic formulation, in particular in a (clear) beverage.

It was found that when a (wing) stirrer, e.g. available from IKA or Ystral, or a rotor stator dispergator, like an Ultra Turrax or Ystral Dispermix, is used for mixing, the obtained compositions according to the invention comprising polyphenols, flavonoids and/or diterpenoid glucosides when combined with other beverage ingredients, resulted in a clear beverage, the polyphenols, flavonoids and/or diterpenoid glucosides remaining stable even at long storage times. However, when using a high pressure homogenizer the polyphenols, flavonoids and/or diterpenoid glucosides in many cases precipitated in the beverages after a short period of storage. Because of this unexpected behavior the inventors believe that a complexing phenomenon of the emulsifying polymer(s) and saponin(s) in the presence of the partially or fully water-miscible solvent(s) and water occurs, the resulting complex stabilizing the polyphenols, flavonoids and/or diterpenoid glucosides in the (food or cosmetic) formulation, in particular in beverages.

Therefore, in a preferred method of preparing a composition, preferably a preferred composition according to the present invention, the mixing is conducted using a stirrer or a rotor stator dispergator.

Another preferred method of preparing a composition according to the present invention comprises the following steps:

(1) providing as components individually or in combination (i) one, two, three or more ingredients selected from the group consisting of polyphenols, flavonoids and/or diterpenoid glucosides, optionally (ii) water, additionally to the water comprised in component (iv), (iii) one partially or fully water-miscible, preferably liquid, solvent or a mixture of partially or fully water-miscible, preferably liquid, solvents, preferably selected from the group consisting of ethanol, propylene glycol (1,2-propanediol), glycerin, triacetin (glycerin triacetate), diacetin (glycerin diacetate) and triethyl citrate, (iv) a solubilization agent (prepared) according to the present invention, in an amount effective to increase the solubility of one or more ingredients of component (i), (2) dissolving component (i) and, optionally, further components in component (iii) to prepare a first solution, (3) dissolving component (iv) and, optionally, further components in component (ii) to prepare a second solution, (4) mixing said first and second solution.

A particularly preferred composition according to the present invention, particularly suitable for the preparation of (clear) beverage formulations, comprises or consists of:

(i) one, two, three or more polyphenols, flavonoids and/or diterpenoid glucosides selected from the group consisting of hesperetin, phloretin, homoeriodictyol, rubusoside and naringin, (iv) a solubilization agent (prepared) according to the present invention comprising (a) gum Arabic, (b) quillaic saponins, (c) propylene glycol and (d) water, preferably in the preferred amounts and ratios indicated hereinbefore or hereinafter, in an amount effective to increase the solubility of one or more ingredients of component (i), (v) citric acid, and optionally (vi) potassium sorbate and/or sodium benzoate.

In a further aspect the present relates to a food or cosmetic formulation, comprising (A) a composition according to the present invention (preferably according to one of the above mention preferred forms) or prepared according to a method according to the present invention (preferably according to one of the above mention preferred forms), and (B) one or more further cosmetic or food ingredients.

The food or cosmetic formulations according to the invention comprise a solubilization agent in accordance with the present invention allowing the incorporation of an increased amount of polyphenols, flavonoids and/or diterpenoid glucosides into said food and cosmetic formulations. The food or cosmetic formulations according to the invention show an improved storage stability (shelf life). The solubilization agents used therein prevent precipitation or recrystallization of (sparingly water soluble) polyphenols, flavonoids and/or diterpenoid glucosides of component (i), as for example occurs during (prolonged) storage.

Cosmetic formulations according to the invention comprising a solubilization agent in accordance of the present additionally provide for a higher bioavailability of the polyphenols, flavonoids and/or diterpenoid glucosides of component (i).

A preferred food formulation according to the present invention comprises a total amount of component(s) (i) in the range of from 0.25 g to 0.005 g per kg solid or semi-solid food formulation or per liter of liquid food formulation, preferably in the range of from 0.15 g to 0.0075, more preferably in the range of from 0.10 g to 0.01 per kg solid or semi-solid food formulation or per liter of liquid food formulation.

These total amounts for component(s) (i) in a preferred food formulation in particular relate to the total amount of hesperetin, phloretin, homoeriodictyol, rubusoside and naringin present in said food formulation, preferably to the total amount of hesperetin, phloretin and homoeriodictyol.

Also preferred food formulations according to the present invention comprise an amount of a composition according to the present invention in the range of from 2.0 g to 0.1 g per kg solid or semi-solid food formulation or per liter of liquid food formulation, preferably in the range of from 1.5 g to 0.2, more preferably in the range of from 1.2 g to 0.3 per kg solid or semi-solid food formulation or per liter of liquid food formulation.

A cosmetic formulation according to the present invention preferably contains a total amount of 0.01 wt. % to 2 wt. %, preferably 0.05 to 1.5 wt. %, but in particular 0.1 wt. % to 1 wt. %, in each case based on the total weight of the cosmetic formulation, of component(s) (i), preferably of skin-lightening or skin-tanning polyphenols, flavonoids and/or diterpenoid glucosides, more preferably of skin-lightening or skin-tanning flavonoids, in particular of naringin.

A preferred (food, preferably beverage) formulation according to the invention (as described above, in particular in a preferred variant) contains one or more sweet-tasting substances, wherein the sweet-tasting substance(s) are preferably selected from the group consisting of:

one or more carbohydrates (sugars) chosen from the group consisting of sucrose, trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin and plant preparations containing one or more of the carbohydrates mentioned (preferably in a proportion of at least 5 wt. %, more preferably at least 15 wt. %), wherein these carbohydrates may also be present as a natural or artificially produced mixture (preferably honey, invert sugar syrup, highly enriched fructose syrups from maize starch [High Fructose Corn Syrup]), one or more sugar alcohols chosen from the group consisting of glycerine, erythritol, threitol, arabitol, ribitol, xylitol, sorbitol, mannitol, maltitol, isomaltitol, dulcitol and lactitol, one or more proteins and/or amino acids from the group consisting of miraculin, monellin, thaumatin, curculin, brazzein, glycine, D-leucine, D-threonine, D-asparagine, D-phenylalanine, D-tryptophan, L-proline or extracts or fractions obtained from natural sources, the extracts or fractions containing these amino acids and/or proteins, one or more sweet substances from the group consisting of magap, sodium cyclamate, acesulfam K, sodium salt of saccharin, aspartame, superaspartame, neotam, alitam, sucralose, stevioside, rebaudioside, lugduname, carrelame, sucrononate, sucrooctate, monatin and phyllodulcin, wherein in case of the naturally occurring sweet substances also extracts or enriched fractions of these extracts may be used, preferably stevia extracts, citrus extracts, buddha tea extracts, and mixtures thereof.

A preferred food, preferably a beverage, formulation according to the invention (preferably as described hereinbefore or hereinafter in a preferred variant) contains one, two, three, four, five, six, seven or more aroma or flavor ingredients, preferably selected from natural flavor oils and/or (natural) aroma substances.

Natural flavor oils optionally included in the compositions or food formulations according to the present invention are preferably selected from essential oils, preferably selected from the group consisting of: aniseed oil; basil oil; bergamot oil; bitter almond oil; camphor oil; lemon oil; eucalyptus oil; geranium oil; grapefruit oil; ginger oil; camomile oil; spearmint oil, caraway oil, lime oil; mandarin oil; clove (blossom) oil, orange oil; peppermint oil; rose oil; rosemary oil; sage oil; yarrow oil; star aniseed oil; thyme oil; vanilla extract; juniper berry oil; wintergreen oil; cinnamon leaf oil; cinnamon bark oil; and fractions thereof.

Individual aroma substances optionally included in the compositions or food formulations according to the present invention are preferably selected from the group consisting of: aliphatic esters (saturated and unsaturated), e.g. ethyl butyrate, allyl caproate; aromatic esters, e.g. benzyl acetate, methyl salicylate; organic aliphatic acids (saturated and unsaturated) e.g. acetic acid, caproic acid; organic aromatic acids; aliphatic alcohols (saturated and unsaturated); cyclic alcohols, e.g. menthol; aromatic alcohols, e.g. benzyl alcohol; aliphatic aldehydes (saturated and unsaturated) e.g. acetaldehyde; aromatic aldehydes, e.g. benzaldehyde; vanillin; ketones, e.g. menthone; cyclic ethers, e.g. 4-hydroxy-5-methylfuranone; aromatic ethers, e.g. p-methoxybenzaldehyde, guaiacol; lactones, e.g. gamma-decalactone; terpenes, e.g. limonene, linalool, terpinene, terpineol, citral.

Particularly preferred flavor directions of food formulations in accordance with the present invention are selected from the group consisting of:

pineapple, apple, apricot, banana, pear, blackberry, lemon, lime, strawberry, grapefruit, blueberry, raspberry, elderberry, currant (red or black), cherry, kiwi, mandarin, mango, orange, passion fruit, peach, prune, melon (water melon, sugar melon or honeydew melon), grape (red or white), plum, chocolate (white, dark, milk and the like), coffee (plain, cappuccino, espresso, latte macchiato and the like), vanillin, vanilla, cardamom, anise, nutmeg, clove, thyme, cinnamon, rum, whisk(e)y, amaretto, beer, white wine, red wine, cognac, irish cream, hazelnut, almond, spearmint, eucalyptus, and peppermint.

The compositions and (food) formulations according to the present invention may include other auxiliary agents, e.g. colorants, pigments, antioxidants, taste correcting agents, (mineral) salts, carbon dioxide, buffers, thickeners and the like.

Food formulations according to the present invention preferably comprise one, two, three or more additional ingredients, preferably selected from the group consisting of:

antioxidants (preferably tocopherol, ascorbic acid), non-proteinogenic amino acids and allied compounds (preferably γ-aminobutyric acid, taurin), bitter substances (preferably quinine, caffeine, limonine, amarogentine, humolone, lupolone, catechol, tannins), mineral salts (preferably sodium chloride, potassium chloride, magnesium chloride, sodium phosphates), enzymatic browning-preventative substances (preferably sulfite, ascorbic acid), essential oils, plant extracts, natural or synthetic colorants or dye pigments (preferably carotinoids, anthocyans, chlorophyll and their derivatives), trigeminally active substances or plant extracts containing such trigeminally active substances (e.g. trans-pellitorin, spilanthol), taste correcting agents, preferably chosen from the group consisting of: nucleotides (e.g. adenosine-5'-monophosphate, cytidine-5'-monophosphate) or their pharmaceutically acceptable salts, lactisoles, sodium salts (e.g. sodium chloride, sodium lactate, sodium citrate, sodium acetate, sodium gluconate), hydroxybenzoic amides according to DE 10 2004 041 496 (preferably 2,4-dihydroxybenzoic vanillylamide, 2,4-dihydroxybenzoic-N-(4-hydroxy-3-methoxybenzyl)amide, 2,4,6-trihydroxybenzoic-N-(4-hydroxy-3-methoxybenzyl)amide, 2-hydroxy-benzoic-N-4-(hydroxy-3-methoxybenzyl)amide, 4-hydroxybenzoic-N-(4-hydroxy-3-methoxybenzyl)amide, 2,4-dihydroxybenzoic-N-(4-hydroxy-3-methoxybenzyl) amide mono-sodium salt, 2,4-dihydroxybenzoic-N-2-(4-hydroxy-3-methoxyphenyl)ethylamide, 2,4-dihydroxybenzoic-N-(4-hydroxy-3-ethoxybenzyl)amide, 2,4-dihydroxybenzoic-N-(3,4-dihydroxybenzyl)amide and 2-hydroxy-5-methoxy-N-[2-(4-hydroxy-3-methoxyphenyl) ethyl]amide(aduncamide), 4-hydroxybenzoic vanillylamide), gamma-aminobutyric acid according to WO 2005/096841 for minimising or masking an unpleasant impression of taste such as bitterness), diacetyl trimers in accordance with WO 2006/058893 and WO 2007/141102 and/or divanillin as described in WO 2004/078302.

The one or more polyphenols, flavonoids and/or diterpenoid glucosides comprising compositions according to the invention may preferably be included into a food or cosmetic formulation. Preferably the food or cosmetic formulation is clear and is most preferably selected from clear beverages (carbonated or not), preferably lemonade, carbonated soft drinks, tea, ice-tea, beer-lemonade mixes, cola, beer-cola mixes, liqueur, whey drink or beverage powders or concentrates for producing such clear beverages or other clear foods like water ice, broth, gummy bear, hard boiled candy, dressing, sauce, fruit jelly or table top sweeteners.

Cosmetic formulations and concentrates for producing cosmetic formulations in accordance with the present invention can be clear or non-clear.

Cosmetic formulations according to the present invention can take the form for example of soap, synthetic detergent, liquid washing, shower and bath preparation, emulsion (as a solution, dispersion, suspension; cream, lotion or milk depending on the production process and ingredients as a W/O, O/W or multiple emulsion, PIT emulsion, emulsion foam, micro-emulsion, nanoemulsion, Pickering emulsion), as an ointment, paste, gel (including hydrogel, hydrodispersion gel, oleogel), oil, toner, balsam, serum, powder, eau de toilette, toilette, eau de cologne, perfume, wax, as a stick, roll-on, (pump) spray, aerosol (foaming, non-foaming or post-foaming), as a foot care product (including keratolytics, deodorants), as a shaving foam or aftershave (balm, lotion) as a depilatory product, hair care product such as e.g. shampoo (including 2-in-1 shampoo), conditioner, hair tonic, hair water, hair rinse, hair cream, pomade, perm and setting lotion, hair smoothing product (detangling product, relaxer), hair strengthener, styling aid (e.g. gel or wax); blonding product, hair dye (e.g. temporary hair dyes, colour rinses, semi-permanent and permanent hair dyes), as nail care products such as e.g. nail polish and nail polish remover, as deodorants and/or antiperspirants; makeup, makeup remover, decorative cosmetics (e.g. powder, eyeshadows, lipstick).

Cosmetic formulations according to the present invention preferably are topical and/or dermatological formulations, preferably for treatment, care and cleaning of the skin and/or hair or as a make-up product in decorative cosmetics. Accordingly, cosmetic formulations of the present invention preferably are selected from the group consisting of: day protection cream, day or night cream, eye cream, sun protection or after-sun lotion, nourishing cream, a care mask, gel pads, facial tonic, moist care and cleaning tissues, cleaning milk, cleaning soap, foam or shower bath, deodorant, antiperspirant, hair shampoo, hair care agent, hair conditioner, hair colorant, hair styling agent and in this case preferably be present as an emulsion, lotion, milk, fluid, cream, hydro dispersion gel, balm, spray, alcoholic or aqueous/alcoholic solution, foam, powder, liquid soap, piece of soap, shampoo, roll-on, stick or make-up. In hair treatment agents, the use is preferably directed at the base of the hair or the scalp.

Clear cosmetic formulations, preferably are selected from the group consisting of clear oral hygiene formulations, in particular mouthwashes or clear (gel) toothpastes.

Thus, the present invention also relates to a food or cosmetic formulation selected from the group consisting of
clear (carbonated) beverages, preferably selected from the group consisting of lemonade, carbonated soft drinks, tea, ice-tea, beer-lemonade mixes, cola, beer-cola mixes, liqueur, whey drink lemonade, tea, beer-lemonade mixtures, cola drinks, beer-cola mixes, liqueur, and whey drinks,
concentrates for producing clear (carbonated) beverages, preferably selected from the group consisting of lemonade, carbonated soft drinks, tea, ice-tea, beer-lemonade mixes, cola, beer-cola mixes, liqueur, whey drink lemonade, tea, beer-lemonade mixtures, cola drinks, beer-cola mixes, liqueur, and whey drinks,
non-beverage clear foods, preferably selected from the group consisting of water ice products, broth, gummy bear, hard boiled candy, dressing, sauce, fruit jelly, and table top sweeteners,
concentrates for producing non-beverage clear foods, preferably for producing non-beverage clear foods selected from the group consisting of water ice products, broth, gummy bear, hard boiled candy, dressing, sauce, fruit jelly, and table top sweeteners,
clear cosmetic formulations, preferably selected from the group consisting of mouthwashes and gel toothpaste,
concentrates for producing clear cosmetic formulations, preferably for producing clear cosmetic formulations selected from the group consisting of mouthwashes and jelly toothpaste,
non-clear cosmetic formulations,
concentrates for producing non-clear cosmetic formulations.

Substances and auxiliaries which may additionally be included in a cosmetic formulation according to the present invention containing a solubilization agent or a composition in accordance with the present invention preferably are selected from the group consisting of:
preservatives, preferably the abrasives, anti-acne agents and agents for sebum reduction mentioned in US 2006/0089413, preferably the agents mentioned in WO 2008/046791 against skin ageing, preferably the antibacterial agents, anti-cellulitis agents, anti-dandruff agents mentioned in WO 2005/123101, preferably the anti-inflammatory agents, irritation-preventing agents, anti-irritants (anti-inflammatory, irritation-inhibiting and irritation-preventing agents) mentioned in WO 2008/046795, preferably the antimicrobial agents mentioned in WO 2007/042472 and US 2006/0089413, preferably the antioxidants mentioned in WO 2005/123101, preferably the adstringents, antiseptic agents, antistatics, binders, buffers, carrier materials mentioned in WO 2005/123101, preferably the chelating agents mentioned in WO 2005/123101, preferably the cell stimulants, cleaning agents, care agents, depilatory agents, surfactant substances, deodorising agents and antiperspirants mentioned in WO 2005/123101, preferably the softeners, emulsifiers mentioned in WO 2005/123101, preferably the enzymes, essential oils mentioned in WO 2005/123101, preferably the insect repellents mentioned in US 2008/0070825, preferably the fibres, film formers, fixing agents, foam forming agents, foam stabilisers, substances for preventing foaming, foam boosters, fungicides, gelling agents and gel-forming agents mentioned in WO 2005/123101, preferably the hair care agents, hair shaping agents, hair smoothing agents, moisture regulators (moisture-dispensing, moisturising and/or moisture-containing substances) mentioned in WO 2005/123101, preferably the osmolytes mentioned in WO 2005/123101, preferably the compatible solutes mentioned in WO 2005/123101, preferably the bleaching agents, strengthening agents, stain-removing agents, optically brightening agents, impregnating agents, dirt-repellent agents, friction-reducing agents, lubricating agents, moisture creams, ointments, opacifying agents, plasticizing agents, covering agents, polishes, brighteners, polymers mentioned in WO 01/76572 and WO 02/15686, preferably the powders, proteins and protein hydrolysates mentioned in WO 2008/046676, preferably the lipid regulating agents, exfoliating agents, skin-calming agents, skin cleaning agents, skin care agents, skin repair agents, preferably containing cholesterol and/or fatty acids and/or ceramides and/or pseudoceramides mentioned in WO 2005/123101 and WO 2008/046676, in this case preferably the skin brightening agents mentioned in WO 2006/053912, preferably the skin protecting agents, skin softening agents, skin cooling agents mentioned in WO 2007/110415, preferably the skin warming agents mentioned in WO 2005/123101, preferably the stabilisers, UV-absorbing agents and UV filters mentioned in WO 2005/123101, preferably the benzylidene-beta-dicarbonyl compounds mentioned in WO 2005/123101, preferably the alpha-benzoyl cinnamic acid nitriles mentioned in WO 2005/107692, preferably the AhR-receptor antagonists mentioned in WO 2006/015954, preferably the detergents, fabric softeners, suspending agents, skin tanning agents mentioned in WO 2007/060256, preferably the thickeners, vitamins mentioned in WO 2006/045760, preferably the oils, waxes and fats mentioned in WO 2005/123101, preferably the phospholipids mentioned in WO 2005/123101, preferably the fatty acids (saturated fatty acids, singly or multiply unsaturated fatty acids, α-hydroxy acids, polyhydroxy fatty acids) mentioned in WO 2005/123101, preferably the liquefiers, dyes and colour-protecting agents and pigments mentioned in WO 2005/123101, preferably the anti-corrosives, flavors and flavor additives and perfumes mentioned in WO 2005/123101, preferably the alcohols and polyols listed in S. Arctander, Perfume and Flavor Chemicals, self-published, Montclair, N.J., 1969 and Surburg, Panten, Common Fragrance and Flavor Materials, 5$^{th}$ Edition, Wiley-VCH, Weinheim 2006, in particular the alcohols and polyols explicitly mentioned in US 2008/0070825, preferably the surfactants mentioned in WO 2005/123101, preferably the animal extracts, yeast extracts, extracts of algae or micro-algae, electrolytes, liquefiers, organic solvents mentioned in WO 2005/123101, preferably those mentioned in WO 2005/123101, or silicones and silicone derivatives, preferably those mentioned in WO 2008/046676.

The present invention in a further aspect also relates to the use of a mixture of:

(a) one emulsifying polymer or a mixture of two, three or more emulsifying polymers, (b) one saponin or a mixture of two, three or more saponins, and (c) one partially or fully water-miscible, preferably liquid, solvent or a mixture of partially or fully water-miscible, preferably liquid, solvents, preferably selected from the group consisting of ethanol, propylene glycol (1,2-propanediol), glycerin, triacetin (glycerin triacetate), diacetin (glycerin diacetate) and triethyl citrate, as solubilization agent for solubilizing polyphenols, flavonoids and/or diterpenoid glucosides in aqueous liquids.

In a further aspect, the present invention also relates to a method for imparting, enhancing and/or modifying the properties of a polyphenol, flavonoid and/or diterpenoid glucoside, wherein a composition (prepared) according to the present invention is added to or mixed with a base formulation of a product.

Further preferred food formulations comprising a composition according to the present invention are confectionaries, bakery products, and pastries. Particularly preferred are food formulations comprising a composition according to the present invention which in turn comprises a solubilization agent according to the present invention including one, two, three or more quillaic saponins. The use of quillaic saponins (i.e. one quillaic saponin or a mixture of two, three or more quillaic saponins) in a confectionary, a bakery product or in pastries, in particular as a solubilization agent for solubilizing polyphenols, flavonoids and/or diterpenoid glucosides in aqueous liquids for use in such a product, is a relevant aspect of the present invention. As to further details of this aspect of the present invention reference is made to the above discussion of food formulations according to the invention, which applies mutatis mutandis.

Other preferred aspects or embodiments of the invention are disclosed in the following examples and the appended claims.

EXAMPLES

The examples are used to explain the invention without thereby restricting the invention. Unless stated otherwise, all data, in particular percentages, refer to the weight.

Example 1

| Ingredient | solubilisate PHL Parts by weight | solubilisate HES Parts by weight |
|---|---|---|
| Water | 132 | 132 |
| Gum Arabic | 36.8 | 36.8 |
| 1,2-Propylene glycol | Ad 1000 | Ad 1000 |
| Quillaia extract (water-content: 72%) | 40 | 40 |
| Phloretin, 5% in 1,2-propylene glycol | 500 | — |
| Hesperetin, 5% in 1,2-propylene glycol | — | 500 |
| Potassium sorbate, 20% in water | 1.84 | 1.84 |
| Citric acid, 50% in water | 4.14 | 4.14 |

Homogenization was carried out by using an Ultra Turrax dispergator at 3000 rpm for 1 minute.

Beverage Example 1:

110 g sugar syrup 71.7° brix
2.5 g/l citric acid anhydrous, crystalline
0.9 g/l lemon flavor, water soluble
Water
0.8 g/l phloretin containing solubilisate PHL of Example 1 (corresponding to 20 ppm of phloretin)

Beverage Example 2, Sugar Free:

300 ppm rebaudioside A
2.5 g/l citric acid anhydrous, crystalline
0.9 g/l lemon flavor, water soluble
Water
0.8 g/l phloretin containing solubilisate PHL of Example 1 (corresponding to 20 ppm of phloretin)

Beverage Example 3, Sugar Reduced:

100 ppm rebaudioside A
70 g sugar syrup 71.7° brix
2.5 g/l citric acid anhydrous, crystalline
0.9 g/l lemon flavor, water soluble
Water
0.8 g/l phloretin containing solubilisate PHL of Example 1 (corresponding to 20 ppm of phloretin)

Beverage Example 4:

110 g sugar syrup 71.7° brix
2.5 g/l citric acid anhydrous, crystalline
0.9 g/l lemon flavor, water soluble Water
0.4 g/l hesperetin containing solubilisate HES of Example 1 (corresponding to 10 ppm of hesperetin)

Beverage Example 5, Sugar Free:

300 ppm rebaudioside A
2.5 g/l citric acid anhydrous, crystalline
0.9 g/l lemon flavor, water soluble
Water
0.4 g/l hesperetin containing solubilisate HES of Example 1 (corresponding to 10 ppm of hesperetin)

Beverage Example 6, Sugar Reduced:

100 ppm rebaudioside A
70 g sugar syrup 71.7° brix
2.5 g/l citric acid anhydrous, crystalline
0.9 g/l lemon flavor, water soluble
Water
0.4 g/l hesperetin containing solubilisate HES of Example 1 (corresponding to 10 ppm of hesperetin)

Example 2

A composition in accordance with the present invention was prepared similar to Example 1 using naringin as component (i). The resulting solubilisate "C" had a content of naringin of 10 wt. %, the amount of propylene glycol was reducing correspondingly.

Example C1

Skin and Hair Browning Hair Conditioner with UV-B/UV-A Protection

| Part | Raw material name (manufacturer) | INCI name | Content wt. % |
|---|---|---|---|
| A | Lanette O (Cognis) | Cetearyl alcohol | 2.50 |
|  | Eumulgin B 2 (Cognis) | Ceteareth-20 | 0.70 |
|  | Neo Heliopan 357 | Butyl methoxy dibenzoylmethane | 0.50 |
|  | Neo Heliopan ® E 1000 (Symrise) | Isoamyl p-methoxycinnamate | 2.00 |
|  | Solubilisate "C" containing Naringin | 4',5,7-Trihydroxyflavone-7-O-neohesperidoside | 1.00 |
| B | Demineralised water | Water (aqua) | Ad 100 |
|  | Crotein Q (Croda) | Hydroxypropyltrimonium hydrolysed collagen | 1.00 |
|  | Dehyquart SP | Quaternium-52 | 0.50 |
|  | Citric acid | Citric acid | 0.13 |
|  | Symrise perfume oil | Fragrance (perfume) | 0.40 |
| C | Phenonip (Clariant) | Phenoxyethanol (and) methylparaben (and) ethylparaben (and) butylparaben (and) propylparaben (and) isobutylparaben | 0.50 |

Heat part A to 70° C. Dissolve the raw materials for part B with the exception of the perfume oil in water, heat to 90° C. and add this solution to part A whilst stirring. Allow the emulsion to cool to 40° C., stirring slowly, and add the perfume oil whilst stirring. After storing for 24 hours, add the Phenoip whilst stirring.

Example C2

Self-tanning Cream O/W

| Part | Raw material name (manufacturer) | INCI name | Content in wt. % |
|---|---|---|---|
| A | Dracorin CE (Symrise) | Glyceryl stearate citrate | 5.00 |
|  | Lanette 16 (Cognis) | Cetyl alcohol | 1.00 |
|  | Isopropyl palmitate (Croda) | Isopropyl palmitate | 4.00 |
|  | PCL Liquid (Symrise) | Cetearyl ethylhexanoate | 3.00 |
|  | Dragoxat EH (Symrise) | Ethylhexyl ethylhexanoate | 3.00 |
|  | Neutral oil | Caprylic/Capric triglyceride | 6.00 |
|  | Solubilisate "C" containing Naringin | 4',5,7-Trihydroxyflavone-7-O-neohesperidoside | 2.00 |
|  | Abil 200 (Degussa-Goldschmidt) | Dimethicone | 0.50 |
| B | Demineralised water | Water (aqua) | Ad 100 |
|  | EDETA BD (BASF) | Disodium EDTA | 0.10 |
|  | Keltrol T (Danby-Chemie) | Xanthan gum | 0.30 |
|  | Glycerine 99.5% | Glycerine | 1.50 |
|  | Hydrolite-5 (Symrise) | Pentylene glycol | 3.50 |
| C | Sepigel 305 | Polyacrylamide, C13-14 isoparaffin, laureth-7 | 1.00 |
| D | Demineralised water | Water (aqua) | 10.00 |
|  | Dihydroxyacetone (Merck) | Dihydroxyacetone | 5.00 |
|  | Ethanol 96% | Ethanol | 2.00 |
| E | Perfume oil (Symrise) | Fragrance | 0.30 |

Heat phase A and B separately to approx. 80° C. Add phase B to phase A without stirring and homogenise. Cool to 50° C. and add phase C whilst stirring and homogenise. Cool to 35° C. and add phase D. Add phase E at room temperature.

The invention claimed is:
1. A clear composition comprising:
  (i) phloretin, hesperetin, homoeriodictyol, rubusoside and/or naringin,
  (ii) water,
  (iii) propylene glycol,
  (iv)(a) gum Arabic, pectin, traganth gum and/or gum Ghatt, and
  (iv)(b) a quillaic saponin,
    wherein the weight ratio of (iv)(a) to (iv)(b) is from 20:1 to 1:2, the composition is free of ethanol, and the composition remains clear without agitation at 25° C. and 1013 mbar for at least 1 year.
2. The composition according to claim 1, wherein the weight ratio of (iv)(a) to (iv)(b) is from 10:1 to 1:2.
3. A clear composition comprising:
  (i) phloretin, homoeriodiclyol, rubsoside and/or naringin,
  (ii) water,
  (iii) propylene glycol,
  (iv)(a) gum Arabic, pectin, traganth gum and/or gum Ghatt, and
  (iv)(b) a quillaic saponin,
    wherein the weight ratio of (iv)(a) to (iv)(b) is from 20:1 to 1:2 the composition remains clear without agitation at 25° C. and 1013 mbar for at least 1 year.
4. The composition according to claim 3, wherein the weight ratio of (iv)(a) to (iv)(b) is from 10:1 to 1:2.

* * * * *

UNITED STATES PATENT AND TRADEMARK OFFICE
CERTIFICATE OF CORRECTION

| | | |
|---|---|---|
| PATENT NO. | : 9,433,235 B2 | Page 1 of 1 |
| APPLICATION NO. | : 13/574102 | |
| DATED | : September 6, 2016 | |
| INVENTOR(S) | : Dirk Schrader et al. | |

It is certified that error appears in the above-identified patent and that said Letters Patent is hereby corrected as shown below:

In the Claims

At Column 18, Claim number 3, Line number 53, please change as follows:
(i) phloretin, homoeriodiclyol, rubusoside and/or naringin, Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*